(12) United States Patent
Park

(10) Patent No.: US 8,552,069 B2
(45) Date of Patent: Oct. 8, 2013

(54) METHOD FOR TREATMENT OF OBESITY, DYSLIPIDEMIA, FATTY LIVER OR INSULIN RESISTANCE SYNDROME COMPRISING CAMPHENE AS ACTIVE INGREDIENT

(75) Inventor: Tae Sun Park, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 17 days.

(21) Appl. No.: 13/256,461

(22) PCT Filed: Dec. 29, 2009

(86) PCT No.: PCT/KR2009/007905
§ 371 (c)(1),
(2), (4) Date: Oct. 21, 2011

(87) PCT Pub. No.: WO2010/107177
PCT Pub. Date: Sep. 23, 2010

(65) Prior Publication Data
US 2012/0035274 A1     Feb. 9, 2012

(30) Foreign Application Priority Data

Mar. 18, 2009   (KR) .................. 10-2009-0022937

(51) Int. Cl.
*A61K 31/125*   (2006.01)
*A61K 36/00*   (2006.01)

(52) U.S. Cl.
USPC ........... 514/692; 514/824; 514/866; 514/909; 424/725

(58) Field of Classification Search
USPC ................. 424/725; 514/692, 824, 866, 909
See application file for complete search history.

(56) References Cited

U.S. PATENT DOCUMENTS

| | | |
|---|---|---|
| 6,455,078 B1 | 9/2002 | Wu |
| 2004/0247669 A1 | 12/2004 | Gin et al. |

FOREIGN PATENT DOCUMENTS

CN    101143172 A   *  3/2008

OTHER PUBLICATIONS

Yasni et al., "Identification of an Active Principle in Essential Oils and Hexane-Soluble Fractions of Curcuma Xanthorrhiza Roxb. Showing Triglyceride-Lowering Action in Rats", Food and Chemical Toxicology, vol. 32, No. 3, pp. 273-278 (1994).*
CN 101143172 A (2008), English Translation.*
Straznicky et al., "Effects of Dietary Weight Loss on Sympathetic Activity and Cardiac Risk Factors Associated with the Metabolic Syndrome," J. Clin. Endocrinol. Metab. 90:5998-6005, 2005.
International Search Report from International Application No. PCT/KR2009/007905, dated Aug. 31, 2010 (date of completion of search) and Sep. 1, 2010 (date of Mailing of Report).

* cited by examiner

*Primary Examiner* — Kevin E Weddington
(74) *Attorney, Agent, or Firm* — Clark & Elbing LLP

(57) ABSTRACT

Disclosed is a composition including camphene as an active ingredient for preventing or treating obesity, dyslipidemia, fatty liver or insulin resistance syndrome. The composition of the present disclosure including camphene as an active ingredient suppresses differentiation of adipocytes, reduces body fat, reduces visceral fat, reduces total cholesterol level, reduces serum triglyceride level and reduces liver tissue triglyceride level, and thus exhibits preventive or therapeutic activity for obesity, hyperlipidemia or fatty liver. Furthermore, the composition of the present disclosure exhibits the effect of improving type 2 diabetes or insulin resistance and related metabolic disease by significantly reducing fasting blood sugar level and blood insulin level. Also, the composition of the present disclosure exhibits the effect of reducing visceral fat by significantly reducing the expression of nuclear transcription factors (C/EBPα and PPARγ2) playing key roles in adipogenesis or their target gene (aP2), the effect of improving chronically activated inflammation in the visceral fat tissue induced by obesity by significantly reducing the expression of cytokines (TNF-α or IL-6) activating inflammation, and the effect of improving suppressed heat generation in the visceral fat tissue induced by obesity by significantly increasing the expression of UCP (UCP1 or UCP3) genes regulating body heat production.

14 Claims, 7 Drawing Sheets

Significantly different from the value for DMSO-treated control cells at $P < 0.01$ by Student's $t$-test.

Different letters above the bar exhibit significant difference at $P < 0.001$ by one-way ANOVA followed by Duncan's multiple range test.

METHOD FOR TREATMENT OF OBESITY, DYSLIPIDEMIA, FATTY LIVER OR INSULIN RESISTANCE SYNDROME COMPRISING CAMPHENE AS ACTIVE INGREDIENT

CROSS-REFERENCE TO RELATED APPLICATIONS

This application is the U.S. national stage filing under 35 U.S.C. §371 of international application PCT/KR2009/007905, filed Dec. 29, 2009, which claims benefit of Korean Patent Application 10-2009-0022937, filed Mar. 18, 2009.

TECHNICAL FIELD

The present disclosure relates to a composition for preventing or treating obesity, hyperlipidemia, fatty liver or insulin resistance syndrome comprising camphene as an active ingredient.

BACKGROUND

As abdominal obesity increases in modern people due to the change in lifestyles, occurrence of metabolic diseases including diabetes, hypertension, dyslipidemia, insulin resistance, etc. is increasing rapidly. These diseases increase the risk of incidence one another and are commonly related to the cause of metabolic changes, such as aging, stress and suppressed immune system.

According to the 2005 Korea National Health and Nutrition Examination Survey, 32% of Korean adults aged 20 years or older turned out to be obese (35.2% of men and 28.3% of women). Infantile obesity is also increasing rapidly among Koreans. In 2005, 11.3% of elementary schoolchildren, 10.7% of middle school students and 16% of high school students were classified to be obese (BMI≥25 $kg/m^2$), and 17% of overweight (BMI≥23 $kg/m^2$) or obese teenagers had metabolic diseases.

Such increase in overweight and obese population leads to increased prevalence of chronic diseases. Actually, the prevalence of hypertension (30.2% in men and 25.6% in women), diabetes (9.0% in men and 7.2% in women) and hypercholesterolemia (7.5% in men and 8.8% in women) in Koreans aged 30 or older in 2005 was very high as compared to other countries. In 2005, deaths caused by diabetes in Korea were 35.5 per 100,000 people, 3-7 times more than those of Japan (5.9), England (7.5) or Germany (16.6). The number of Korean diabetic patients is expected to grow from 3,000,000 to 5,450,000 in 2030, meaning that 10% of Koreans will be diabetic patients.

According to the Korea Institute for Health and Social Affairs, the socioeconomic loss caused by obesity and obesity-related complications in 2006 is estimated at 2.1 trillion won including medical cost and indirect cost such as loss of earning. Thus, in 2010, the Korean government has decided to reduce the obesity rate down to 20% in men and 15% in youth, and is exploring ways to accurately define and diagnose obesity and metabolic diseases.

A lot of products for obesity treatment are imported from abroad and marketed in Korea. Among them, Xenical, Reductil and Exolise are well-known anti-obesity drugs. Xenical, which contains orlistat as main ingredient, is the world's first obesity treatment drug. It reduces absorption of fat by inhibiting lipase, and is effective in reducing total cholesterol and LDL cholesterol level, improving blood sugar and reducing blood pressure. Reductil, which contains sibutramine as main ingredient, was approved by FDA in 1997 and is marketed in more than 30 countries. The drug is effective in stimulating sympathetic nerves, reducing appetite and inducing satiety by keeping the level of serotonin and noradrenaline in the sympathetic nervous system high. And, Exolise is a non-prescription semiproduct imported from France. It increases body heat production and basal metabolic rate, and reduces fat absorption by about 30% by inhibiting lipase, and increase energy consumption by increasing the production of noradrenaline.

Although obesity can best treated by a combination of diet, exercise and behavior modification, it requires a lot of time and efforts and is difficult to put into practice. For this reason, obesity drugs or diet products are used a lot. However, orlistat is known to have side effects such as steatorrhea, production of bowel gas, abdominal inflation, etc., and sibutramine is known to have side effects such as headache, thirst, loss of appetite, insomnia, constipation, etc. Also, orlistat inhibits absorption of vitamin E and vitamin D, and phentermine and sibutramine can increase heart rate and cause tachycardia or dizziness.

Diabetes is caused by insufficient production or action of insulin. With prolonged metabolic disorder including hyperglycemia, it is highly likely to vascular complications. The number of diabetic patients is increasing consistently in tandem with the population aging and the change in lifestyles. In 1985, the number of diabetic patients in the world was 30 million, but is estimated at about 220 million in 2010. Particularly in industrialized countries, the number of diabetic patients is estimated to reach 10% of the total population. According to data from the Korea Institute of Science & Technology Evaluation and Planning, the global diabetes drug market is valued at about 11.8 billion dollars in 2005, increasing 12% year on year, and the US market of blood sugar measurement and insulin has grown from 2.6 billion dollars in 2004 to 3 billion dollars in 2005 by more than 15%. According to the IDF report, the global diabetes drug market is expected to grow by about 25% until 2025. And, according to the ADA report, the direct and indirect medical cost due to type 2 diabetes in the US in 2002 is estimated over 132 billion dollars.

While metformin- and thiazolidinedione (TZD)-based drugs as currently available type 2 diabetes drugs show considerable efficacy, they do not cure the fundamental cause of diabetes such as the onset of insulin resistance and several side effects are reported. Therefore, development of a more effective and safe drug capable of resolving the insulin resistance problem is necessary. At present, the ultimate aim of diabetic treatment is to consistently maintain a normal blood glucose level. It is because many animal and clinical experiments suggest that most diabetic complications are caused by metabolic disorders due to prolonged high blood glucose level and they can be prevented or delayed through strict control of blood sugar. Clinically used diabetes drugs can be classified largely into 1) drugs promoting the secretion of insulin, 2) drugs enhancing the sensitivity of insulin receptors, and 3) drugs suppressing glycolysis and thus reducing glucose absorption. Insulin exhibits the same physiological action as that in the body, but it has to be administered by injection and is associated with the insulin resistance problem. Sulfonylureas (glibenclamide, glipizide, gliquidone, etc.) are orally administrable and inexpensive, but they may induce hypoglycemia and loss of insulin-secreting ability. Biguanides (metformin, phenformin, etc.) suffer the problems of gastrointestinal side effects and nephrotoxicity. Glitazones (troglitazone, pioglitazone, rosiglitazone, etc.) were withdrawn from the market due to side effects such as heart failure, anemia, etc. Thus, development of medications ensuring both safety and efficacy is imminent.

As the synthetic drugs show limitations in side effects, new drugs derived from natural sources are drawing attentions. The inventors of the present disclosure have searched for obesity-suppressing active substances from plant sources and have taken notice of the monoterpene compound camphene, which is included in various plants.

Camphene is a constituent of essential oils from such plants as rosemary, camphor tree, nutmeg, tumeric, peppermint, ginger, pine tree, silver magnolia, cnidium, with molecular formula $C_{10}H_{16}$ and molecular weight 136.2. Camphene has long been used as food additive for flavoring. According to a recent report about the physiological activity of camphene, it has antioxidative, anti-inflammatory and antimicrobial activities (Antioxidative properties of the essential oil from *Pinus* mugo, *J Argic Food Chem*, 51(26): 7576-7582, 2003). Camphene has been proven to have anti-inflammatory effect by suppressing the activity of the inflammation-inducing factor NF-κB in mouse macrophage cells (RAW 264.7) (Anti-inflammation activity of fruit essential oil from *Cinnamomum insularimontanum* Hayata, *Bioresource Technology* 99: 8783-8787, 2008). Also, camphene has been shown to have antimicrobial activity by inhibiting growth of Gram-positive bacteria, Gram-negative bacteria and fungi (Chemical composition and antimicrobial activity of essential oil from cones of *Pinus koraiensis*, *J Microbiol Biotechnol*, 18(3): 497-502, 2008). Camphene is listed in the KFDA food additive database for use as flavoring agent and thus can be used as a.

U.S. Pat. No. 7,071,195 discloses a method for treating obesity using amine and amide derivatives acting as ligands for the neuropeptide Y Y5 receptor. U.S. Pat. No. 7,022,722 discloses thiazolidinedione analogs for the treatment of diabetes, hyperlipidemia or obesity.

U.S. Pat. No. 6,987,131 discloses compositions for treating hyperlipidemia, comprising phenylacetylglutamine, phenylacetylisoglutamine or phenylacetic acid. U.S. Pat. No. 6,942,967 discloses the use of the apobec-1 protein for targeting atherosclerosis, hyperlipidemia, obesity and diabetes.

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THE INVENTION

The inventors of the present disclosure have made efforts to develop substances having preventive or therapeutic activity for metabolic diseases including obesity, dyslipidemia and/or fatty liver from natural sources. As a result, they have found out that camphene, included in various plants, have such activity.

The present disclosure is directed to providing a composition for preventing or treating obesity, dyslipidemia, fatty liver or insulin resistance syndrome, containing camphene as an active ingredient.

The present disclosure is also directed to providing a method for preventing or treating a metabolic disease selected from a group consisting of obesity, dyslipidemia, fatty liver and insulin resistance syndrome.

Other features and aspects will be apparent from the following detailed description, drawings, and claims.

In one general aspect, the present disclosure provides a composition for preventing or treating a metabolic disease selected from a group consisting of obesity, dyslipidemia, fatty liver and insulin resistance syndrome, comprising camphene as an active ingredient.

In another general aspect, the present disclosure provides a method for preventing or treating a metabolic disease selected from a group consisting of obesity, dyslipidemia, fatty liver and insulin resistance syndrome, comprising administering a composition comprising camphene as an active ingredient to a subject.

The inventors of the present disclosure have made efforts to develop substances having preventive or therapeutic activity for metabolic diseases including obesity, dyslipidemia and/or fatty liver from natural sources. As a result, they have found out that camphene, included in various plants, have such activity.

As demonstrated in the following examples, camphene suppresses differentiation into adipocytes, reduces body fat, reduces visceral fat, lowers total cholesterol level, and lowers triglyceride level in serum and liver tissue, thus significantly improving obesity induced by high-fat diet. Also, since camphene significantly lowers fasting blood sugar level and blood insulin level, it has the effect of improving type 2 diabetes or insulin resistance and related metabolic inflammatory responses.

As used herein, the term "dyslipidemia" refers to an abnormal amount of lipids in the blood, including hyperlipidemia, hypercholesterolemia, hypertriglyceridemia, hypoalphalipoproteinemia and disorder of lipoprotein metabolism.

As used herein, the term "hyperlipidemia" refers to the condition of abnormally elevated levels of lipids in the blood, resulting from abnormal metabolism of lipids including triglyceride and cholesterol. More specifically, it refers to the condition where the level of lipid components such as triglyceride, LDL cholesterol, phospholipid, free fatty acid, etc. in the blood is elevated and includes the commonly occurring hypercholesterolemia or hypertriglyceridemia.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

As used herein, the term "diabetes" refers to a chronic disease characterized by relative or absolute lack of insulin, leading to glucose intolerance. The term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or insulin resistance.

As used herein, the term "insulin resistance" refers to a physiological condition where insulin becomes less effective at lowering blood sugars and glucose is not effectively combusted by cells. Under high insulin resistance, the body may produce too much insulin, leading to hypertension or dyslipidemia as well as heart disease, diabetes, or the like. Especially, in type 2 diabetes, muscle and adipose tissues do not notice the increase of insulin.

As used herein, the term "insulin resistance syndrome" refers to a combination of disorders caused by insulin resistance, characterized by resistance of cells against the action of insulin, hyperinsulinemia, increase of very-low-density lipoprotein (VLDL) and triglyceride, decrease of high-density lipoprotein (HDL), hypertension, or the like. It is recognized as a risk factor for cardiovascular diseases and type 2 diabetes (Reaven G M., Role of insulin resistance in human disease, *Diabetes*, 37: 1595-607 (1988)). Also, insulin resistance is known to increase oxidative stress and change the signal transduction system in cells along with other risk factors such as hypertension, diabetes, smoking, etc., thus inducing inflammatory responses and leading to atherosclerosis (Freeman B A et al., Biology of disease: free radicals and tissue injury, *Lab. Invest.* 47: 412-26 (1982), Kawamura M et al., Pathophysiological concentrations of glucose promote oxidative modification of low density lipoprotein by a superoxide-dependent pathway, *J. Clin. Invest.* 94: 771-8 (1994)).

As used herein, the term "metabolic disease" refers to a group of diseases involving disorders of metabolism which are risk factors of various cardiovascular diseases and type 2 diabetes. It includes insulin resistance and complex and diverse metabolic disorders related thereto. In 1988, Reaven proposed insulin resistance as the factor underlying these disorders and named the constellation of abnormalities insulin resistance syndrome. However, in 1998, the World Health Organization (WHO) introduced the term metabolic syndrome or metabolic disease since all the aspects of the symptoms cannot be explained by insulin resistance.

The active ingredient of the present disclosure, camphene, is a constituent of essential oils from plants such as rosemary, camphor tree, nutmeg, tumeric, peppermint, ginger, pine tree, silver magnolia, cnidium. Its molecular formula is $C_{10}H_{16}$ and its molecular weight is 136.2. Camphene exists either as (+)-camphene represented by Chemical Formula 1 or as (−)-camphene represented by Chemical Formula 2:

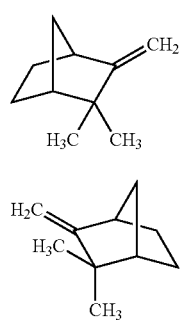

The composition of the present disclosure comprising camphene as an active ingredient has activities of improving various metabolic diseases, e.g., obesity, dyslipidemia, fatty liver or insulin resistance syndrome. The composition of the present disclosure can prevent or treat metabolic diseases with various activities.

Typical Five Examples are as Follows:

In an embodiment, the composition of the present disclosure exhibits the preventive or therapeutic activity by significantly reducing the differentiation of adipocytes. As described in the Examples section, the composition of the present disclosure exhibits preventive or therapeutic activity for metabolic diseases by significantly reducing the differentiation of preadipocytes in a concentration-dependent manner (see FIG. 1).

In another embodiment, the composition of the present disclosure exhibits the preventive or therapeutic activity by significantly reducing the level of fats in the serum or liver, more specifically the level of triglyceride, cholesterol or free fatty acid in the serum or liver. As described in the Examples section, the composition of the present disclosure exhibits preventive or therapeutic activity for metabolic diseases by significantly reducing triglyceride level, total cholesterol level, LDL+VDL cholesterol level, arteriosclerotic index and free fatty acid level in the serum as well as triglyceride level, cholesterol level and free fatty acid level in the liver (see Tables 2 and 3).

In another embodiment, the composition of the present disclosure exhibits the preventive or therapeutic activity by significantly reducing the visceral fat mass, specifically the weight of epididymal fat, perirenal fat, mesenteric fat or retroperitoneal fat. As described in the Examples section, the composition of the present disclosure exhibits preventive or therapeutic activity for metabolic diseases by significantly reducing the weight of total visceral fat, epididymal fat, perirenal fat, mesenteric fat and retroperitoneal fat (see FIG. 3).

In another embodiment, the composition of the present disclosure exhibits the preventive or therapeutic activity by significantly reducing glucose level or insulin level in the serum. As described in the Examples section, the composition of the present disclosure exhibits preventive or therapeutic activity for metabolic diseases by significantly reducing fasting blood sugar level and blood insulin level (see Table 2).

In another embodiment, the composition of the present disclosure exhibits the preventive or therapeutic activity by (i) significantly reducing the expression of nuclear transcription factors playing an important role in adipogenesis in visceral fat tissue and their target genes, (ii) significantly reducing the expression of cytokines activating inflammation in visceral fat tissue, and (iii) significantly increasing the expression of uncoupling proteins (UCPs) regulating body heat production in visceral fat tissue. As described in the Examples section, the composition of the present disclosure exhibits preventive or therapeutic activity for metabolic diseases by (i) reducing the expression of C/EBPα, PPARγ2 and/or their target gene aP2 in mouse visceral fat tissue (see FIGS. 5a and 5b), (ii) reducing the expression of tumor necrosis factor-alpha (TNF-α) and/or interleukin-6 (IL-6) (see FIGS. 6a and 6b), and (iii) increasing the expression of uncoupling protein 1 (UCP1) and/or uncoupling protein 3 (UCP3) (see FIG. 7).

In a specific embodiment of the present disclosure, the composition of the present disclosure is used to prevent or treat dyslipidemia, more specifically hyperlipidemia.

As described in the Examples section, the administration of the composition of the present disclosure shows remarkably effect on dyslipidemia, especially hyperlipidemia, of reducing triglyceride level by 69%, total cholesterol level by 60%, LDL+VLDL cholesterol level by 79% and free fatty acid level by 86% in the serum, as compared to the high-fat diet group (see Table 2).

In a specific embodiment of the present disclosure, the composition of the present disclosure is used to prevent or treat insulin resistance syndrome, more specifically obesity, hypertension, arteriosclerosis, hyperlipidemia, hyperinsulinemia, non-alcoholic fatty liver or type 2 diabetes caused by insulin resistance.

As described in the Examples section, the administration of the composition of the present disclosure shows effect of improving insulin resistance syndrome and related metabolic diseases by reducing fasting blood sugar level by at least 10%, blood insulin level by 32% and insulin resistance index (IRI) by 40%, as compared to the high-fat diet group (see Table 2).

In a specific embodiment of the present disclosure, the composition of the present disclosure reduces the expression of CCAAT/enhancer binding protein alpha (C/EBPα), peroxisome proliferator-activated receptor gamma 2 (PPARγ2) and/or adipocyte protein 2 (aP2).

As described in the Examples section, the administration of the composition of the present disclosure is effective in reducing visceral fat by significantly reducing the expression of the nuclear transcription factors (C/EBPα and PPARγ2) and/or their target gene (aP2), which increased in visceral fat tissue due to high-fat diet (see FIGS. 5a and 5b).

In a specific embodiment of the present disclosure, the composition of the present disclosure reduces the expression of tumor necrosis factor-alpha (TNF-α) and/or interleukin-6 (IL-6).

As described in the Examples section, the administration of the composition of the present disclosure shows remarkable effect of improving chronically activated inflammation in visceral fat tissue induced by obesity by reducing the expression of TNFα and/or IL-6, which increased due to high-fat diet, back to the level comparable to that of the ND group (see FIGS. 6a and 6b).

In a specific embodiment of the present disclosure, the composition of the present disclosure increases the expression of uncoupling protein 1 (UCP1).

As described in the Examples section, the administration of the composition of the present disclosure shows remarkable effect of improving heat production in visceral fat tissue, which decreased due to high-fat diet, by increasing the expression of UCP1 or UCP3 (see FIG. 7).

In a specific embodiment of the present disclosure, the camphene is one included in the extract or fraction of a plant.

The plant may be any one containing camphene without special restriction. Specifically, camphene may be extracted or fractionated from rosemary, camphor tree, nutmeg, tumeric, peppermint, ginger, pine tree, silver magnolia, cnidium, *Abies alba* (Christmas tree), *Abies balsamea* (balm of Gilead), *Abies sibirica* (Siberian fir), *Achillea millefolium* (carpenter's weed), *Acorus calamus* (calamus rhizome), *Aesculus hippocastanum* (horse chestnut), *Agastache foeniculum* (anise hyssop), *Agathosma betulina* (bookoo), *Ageratum conyzoides* (Appa grass), *Aloysia citrodora* (lemon verbena), *Alpinia galangal* (Chinese ginger), *Alpinia officinarum* (Chinese ginger), *Anatherum muricatum* (Cus-Cus), *Andropogon nardus* (Ceylon citronella), *Anethum graveolens* (dill), *Angelica archangelica* (angelica), *Aniba duckei* (bois de rose), *Apium graveolens* (celery), *Aralia cordata* (Japanese spikenard), *Artemisia absinthium* (absinth), *Artemisia annua* (annual mugwort), *Artemisia capillaris* (capillaris), *Artemisia dracunculus* (French tarragon), *Artemisia vulgaris* (Chinese moxa), *Aurantium* var. *Citrus* (bigarade orange), *Boldea fragrans* (boldo), *Boswellia carteri* (frankincense), *Bosweffia glabra* (boswellia), *Callicarpa americana* (American beauty berry), *Cannabis sativa* (hemp), *Capsicum annuum* (African pepper), *Carum carvi* (caraway), *Centella asiatica* (Asiatic pennywort), *Chamaemelum nobile* (chamomile), *Chrysanthemum balsamita* (alecost), *Chrysanthemum parthenium* (bachelor's button), *Cinnamomum aromaticum* (bastard cinnamon), *Cinnamomum camphora* (camphor tree), *Cinnamomum verum* (Ceylon cinnamon), *Cistus creticus* (ambreine), *Citrus aurantiifolia* (Egyptian lime), *Citrus limon* (Canton lemon), *Citrus reticulata* (Mandarin orange), *Citrus sinensis* (blood orange), *Citrus×paradisi* (grapefruit pericarp), *Coleus barbatus, Coriandrum sativum* (Chinese parsley), *Croton eleuteria* (cascarilla), *Cuminum cyminum* (cumin), *Curcuma longa* (turmeric), *Cymbopogon citratus* (citronella), *Cyperus rotundus* (coco-grass), *Daucus carota* (wild carrot), *Dictamnus albus* (akgiritotu), *Elettaria cardamomum* (cardamom), *Elsholtzia ciliata* (elsholtzia), *Eucalyptus camaldulensis* (Murray red gum), *Eucalyptus citriodora* (citron-scented gum), *Eucalyptus globulus* (Australian fever tree), *Ferula gummosa* (galbanum), *Foeniculum vulgare* (bitter fennel), *Glechoma hederacea* (alehoof), *Gossypium* sp. (cotton), *Helianthus annuus* (annual sunflower), *Houttuynia cordata* (dokudami), *Hypericum perforatum* (amber), *Hyptis suaveolens* (wild hops), *Hyssopus officinalis* (azob), *Icimum gratissimum* (hoary basil), *Illicium verum* (Ba Jiao Hui Xiani), *Juniperus communis* (common juniper), *Juniperus sabina* (savin), *Lantana camara* (Bahama tea), *Larrea tridentata* (chaparral), *Laurus nobilis* (bay laurel), *Lavandula angustifolia* (common lavender), *Lavandula latifolia* (aspic), *Lavandula×intermedia* (bastard lavender), *Levisticum officinale* (lovage), *Lindera benzoin* (Benjamin bush), *Lycopus europaeus* (bugleweed), *Magnolia denudata* (Hsin-I), *Magnolia officinalis* (houpu), *Marrubium vulgare* (common horehound), *Melaleuca alternifolia* (narrow-leaved paperbark tea-tree), *Melaleuca cajuputi* (broadleaf paperbark), *Mentha aquatica* (horse mint), *Mentha arvensis piperascens* (American corn mint), *Mentha longifolia* (biblical mint), *Mentha pulegium* (European pennyroyal), *Mentha spicata* (fish mint), *Micromeria juliana* (micromeria), *Monarda citriodora* (lemon mint), *Monarda clinopodia* (clinopod bergamot), *Monarda didyma* (bee balm), *Monarda punctata* (horse mint), *Myristica fragrans* (mace), *Myrtus communis* (common myrtle), *Ocimum basilicum* (basil), *Ocimum gratissimum* (African basil), *Oenanthe aquatica* (fine-leaved water dropwort), *Oenanthe javanica* (Chinese celery), *Origanum onites* (oregano), *Origanum syriacum* (Bible hyssop), *Origanum vulgare* (common marjoram), *Origanum vulgare hirtum* (Greek oregano), *Pastinaca sativa* (parsnip), *Perilla frutescens* (beefsteak plant), *Petroselinum crispum* (common parsley), *Pimpinella anisum* (anise), *Pinus australis* (longleaf pine), *Pinus montana* (dwarf mountain pine), *Pinus roxburghii* (Chir pine), *Pinus silvestris* (pine), *Piper nigrum* (black pepper), *Pogostemon cablin* (Indian patchouli), *Psidium guajava* (common guava), *Ptychopetalum olacoides* (Muira Puama), *Pycnanthemum muticum* (blunt mountainmint), *Pycnanthemum virginianum* (Virginia mountainmint), *Ribes nigrum* (blackcurrant), *Rosa×damascena* (Damask rose), *Rosmarinus officinalis* (rosemary), *Salvia fruticosa* (Greek oregano), *Salvia officinalis* (broadleaf sage), *Salvia sclarea* (clary), *Sassafras albidum* (ague tree), *Satureja montana* (savory), *Satureja thymbra* (goat oregano), *Schinus molle* (California peppertree), *Tagetes filifolia* (Irish lace), *Tagetes minuta* (Aztec marigold), *Teucrium scorodonia* (germander), *Thuja occidentalis* (American arborvitae), *Thymus capitatus* (headed savory), *Thymus mastichina* (mastic thyme), *Thymus serpyllum* (Breckland thyme), *Thymus vulgaris* (common thyme), *Thymus×citriodorus* (Funk's thyme), *Thymus zygis* (Spanish thyme), *Trachyspermum ammi* (ajwain), *Valeriana officinalis* (common valerian), *Vitex agnus-castus* (agnus castus), *Zingiber officinale* (ginger), etc.

The extract of the camphene-containing plant can be obtained by extracting the plant using a commonly used extraction solvent. Specifically, (a) $C_1$-$C_4$ anhydrous or hydrous lower alcohol (e.g., methanol, ethanol, propanol, butanol, n-propanol, isopropanol, n-butanol, etc.), (b) a mixture solvent of the lower alcohol with water, (c) acetone, (d) ethyl acetate, (e) chloroform, (f) 1,3-butylene glycol, (g) hexane, (h) diethyl ether, (i) butyl acetate or (j) water may be used as the extraction solvent.

The fraction of the camphene-containing plant means a more isolated/purified form of the plant extract obtained by further isolation/purification. For example, the camphene-containing plant fraction includes ones obtained by passing the plant extract through an ultrafiltration membrane with a predetermined molecular weight cut-off value, separating through various chromatographic (based on size, charge, hydrophobicity or affinity) techniques, and purifying through various methods.

Also, the camphene may be chemically synthesized.

In a specific embodiment of the present disclosure, the camphene may be one prepared via chemical synthesis in addition to one isolated from the plant.

In another aspect, the present disclosure provides a camphene-containing pharmaceutical composition or food composition for preventing or treating a metabolic disease selected from obesity, dyslipidemia, fatty liver and insulin resistance syndrome.

When the composition of the present disclosure is prepared as a pharmaceutical composition, the pharmaceutical composition of the present disclosure may comprise a pharmaceutically acceptable excipient. The pharmaceutically acceptable excipient included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to above-described components, a lubricant, a wetting agent, a sweetener, a fragrance, an emulsifier, a suspending agent, a preservative, or the like. Suitable pharmaceutically acceptable excipients and formulations are described in detail in Remington's Pharmaceutical Sciences (19th ed., 1995).

The pharmaceutical composition of the present disclosure may be administered orally or parenterally. Specifically, it may be administered orally.

An appropriate dosage of the pharmaceutical composition of the present disclosure may be determined variously depending on such factors as preparation method, administration method, age, body weight and sex of the patient, pathological condition, diet, administration time, administration route, excretion rate or response sensitivity. Specifically, the dosage of the pharmaceutical composition of the present disclosure for an adult may be 0.001-100 mg/kg.

The pharmaceutical composition of the present disclosure may be prepared into a unit dosage form or multiple dosage form along with a pharmaceutically acceptable excipient and/or carrier according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

When the composition of the present disclosure is prepared as a food composition, the pharmaceutical composition of the present disclosure may comprise, in addition to camphene as the active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.]) or a synthetic flavor (saccharin, aspartame, etc.).

For example, when the food composition of the present disclosure is prepared as a drink, it may further comprise, in addition to camphene as the active ingredient, citric acid, high-fructose corn syrup, sugar, glucose, acetic acid, malic acid, fruit juice, eucommia extract, jujube extract, licorice extract, or the like.

BRIEF DESCRIPTION OF THE DRAWINGS

FIG. 5a shows RT-PCR analysis result for C/EBPα, PPARγ2 and aP2, and FIG. 5b shows relative expression of the genes. Data were normalized to GAPDH mRNA levels and were expressed as relative values to the ND group. Data from three independent experiments for 8 mice were represented as mean±SEM. The letters a, b and c exhibit significant difference between test groups at $P<0.05$ by analysis of variance (ANOVA) followed by Duncan's multiple range test.

FIG. 6a shows RT-PCR analysis result for TNFα and IL-6, and FIG. 6b shows relative expression of the genes. Data were normalized to GAPDH mRNA levels and were expressed as relative values to the ND group. Data from three independent experiments for 8 mice were represented as mean±SEM. The letters a and b exhibit significant difference between test groups at $P<0.05$ by analysis of variance (ANOVA) followed by Duncan's multiple range test.

The examples and experiments will now be described. It will be apparent to those skilled in the art that the following examples and experiments are for illustrative purposes only and not intended to limit the scope of this disclosure.

EXAMPLES

Example 1

Camphene's Effect of Suppressing Differentiation of Mouse 3T3-L1 Cells into Adipocyte Cell Culturing and Oil Red O Staining Mouse 3T3-L1 cells were used to investigate the effect of camphene on differentiation and growth of adipocytes. The preadipocytes, 3T3-L1 cells, were seeded on a 12-well plate and cultured to confluency using Dulbecco's modified Eagle's medium (DMEM) containing 1% penicillin-streptomycin, 1% nonessential amino acid and 10% fatal bovine serum (FBS), in a 5% $CO_2$ incubator at 37° C. The 3T3-L1 cells grown to confluency were cultured for 2 days in a medium containing MDI (0.5 mM isobutylmethylxanthine, 1 μM dexamethasone and 1 μg/mL insulin) to differentiate them into adipocytes. Then, the cells were further cultivated in DMEM containing 1 μg/mL insulin to differentiate them into mature adipocytes. The cells were further cultured for 10 more days while replacing DMEM every other day to obtain fully differentiated adipocytes.

From the first day when MDI was added to the 3T3-L1 cells, camphene was treated at concentrations of 0.1, 1, 10, 50 and 100 μM with 2-day intervals. (±)-Camphene purchased from Sigma-Aldrich was used after being dissolved in DMSO. Only DMSO was added to the negative control group. After culturing for a total of 14 days, the medium was removed when the differentiation was completed and lipid droplets in the differentiated adipocytes were stained. For this, the cells were washed twice with phosphate buffered saline (PBS), fixed in 10% buffered neutral formalin (BNF) for 1 hour, washed once again with PBS, stained for 1 hour by adding 1 mL of Oil Red O, which specifically stains fat red, on the 12-well plate, and washed twice with distilled water.

In order to measure the level of triglyceride contained in the differentiated 3T3-L1 cells, the stained lipid droplets were dissolved in 1 mL of isobutanol and OD value was measured at 600 nm.

Camphene's Ability to Suppress Differentiation of Adipocytes

Figure 1A:
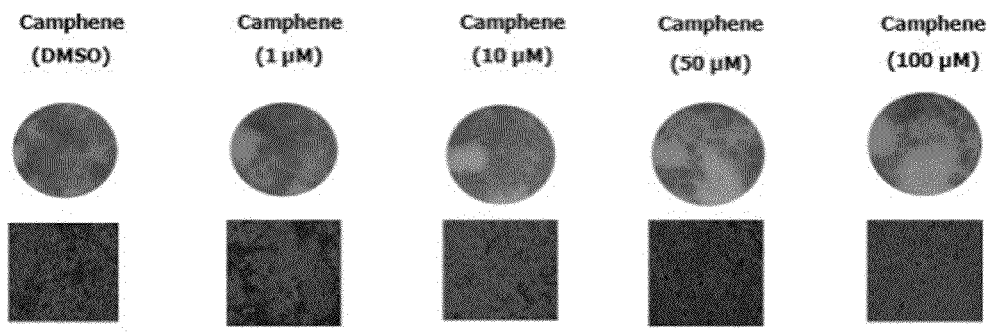
FIGS. 1a-1b show the camphene's effect of suppressing differentiation of 3T3-L1 cells into adipocytes.
Figure 1B:
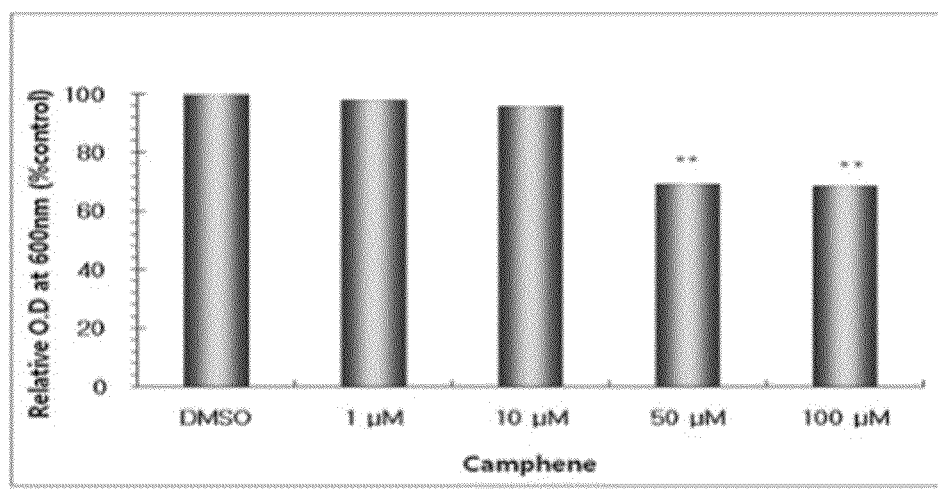

As shown in FIG. 1a, the treatment of the 3T3-L1 cells with camphene reduced the differentiation of the preadipocytes in a concentration-dependent manner. When the amount of the fats stained with Oil Red O was quantitated by spectrophotometry, the OD value also decreased in a concentration-dependent manner (FIG. 1b).

Example 2

Camphene's Effect of Reducing Body Weight and Visceral Fat in Mouse

Preparation of Test Diet and Breeding of Test Animals

The obesity-inducing diet used in this example was high-fat diet (HFD: 40% fat calorie, 17 g lard+3% corn oil/100 g diet). Camphene-containing diet had the same composition as HFD, except that camphene was included at 0.2%. Normal diet (ND) was prepared with the composition of AIN-76 rodent diet (American Institute of Nutrition, Report of the American Institute of Nutrition ad hoc committee on standards for nutritional studies. *J. Nutr.* 107: 1340-1348, 1977) (see Table 1). (±)-Camphene was purchased from Sigma-Aldrich.

TABLE 1

Composition of test diets

| Ingredients (g/kg diet) | Normal diet (ND) | Control diet (HFD) | Camphene-containing diet (Camphene) |
|---|---|---|---|
| Casein | 200 | 200 | 200 |
| D/L-Methionine | 3 | 3 | 3 |
| Corn starch | 150 | 111 | 110 |
| Sucrose | 500 | 370 | 370 |
| Cellulose | 50 | 50 | 50 |
| Corn oil | 50 | 30 | 30 |
| Lard | — | 170 | 170 |
| Vitamin complex | 10 | 12 | 12 |

TABLE 1-continued

Composition of test diets

| Ingredients (g/kg diet) | Normal diet (ND) | Control diet (HFD) | Camphene-containing diet (Camphene) |
|---|---|---|---|
| Mineral complex | 35 | 42 | 42 |
| Choline bitartrate | 2 | 2 | 2 |
| Cholesterol | — | 10 | 10 |
| tert-Butylhydroquinone | 0.01 | 0.04 | 0.04 |
| Camphene | — | — | 2.00 |
| Total (g) | 1,000 | 1,000 | 1,000 |
| Fat (% calorie) | 11.5 | 39.0 | 39.0 |
| Total calorie (kJ/kg diet) | 16,439 | 19,315 | 19,315 |

5-week-old male C57BL/6J mice (Orient, Korea) were accustomed to the laboratory environment for 1 week while feeding solid feed. Then, they were randomly divided into high-fat diet control group and test group and bred for a total of 10 weeks. The diet was given between 10 and 11 a.m. every day together with water. Diet intake was measured every day and body weight was measured once in 3 days. In order to avoid transient body weight increase after feed intake, body weight was measured 2 hours after removing the feed. Feeding efficiency was calculated by dividing accumulated body weight gain during the test period, i.e. from the test diet was given first until the day when the mouse was sacrificed, by total diet intake. After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes to separate the serum.

Body Weight and Visceral Fat Weight

Figure 2:
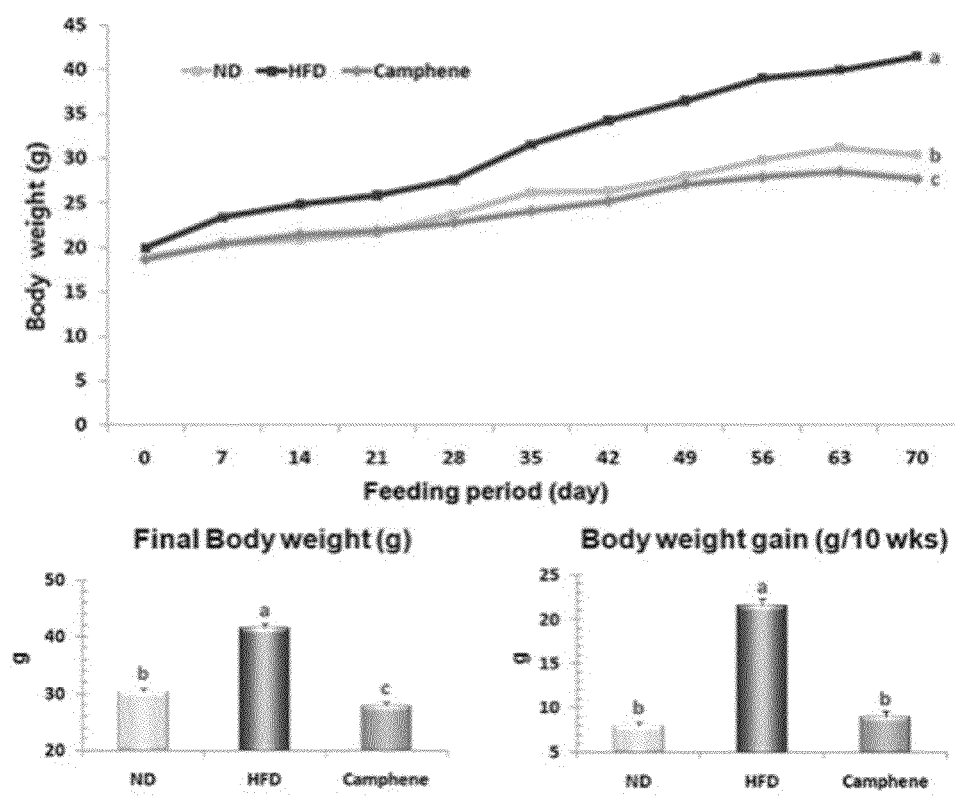
FIG. 2 shows body weight and body weight gain of mice that were given test diets. Gray line and bars denote normal diet group (ND), black line and bars denote high-fat diet control group (HFD), and orange line and bars denote camphene-administered group. The letters a, b and c exhibit significant difference between test groups at $P<0.001$ by analysis of variance (ANOVA) followed by Duncan's multiple range test.

After 10 weeks, the camphene-administered group showed significantly lower final body weight (33%) and accumulated body weight gain (58%) as compared to the high-fat die control group (HFD) (see FIG. 2).

Figure 3:
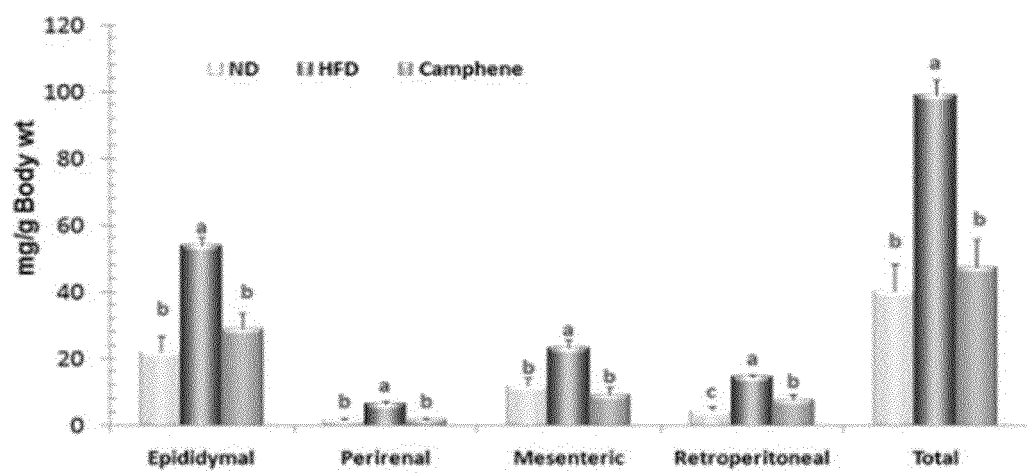
FIG. 3 shows the weight of epididymal fat, perirenal fat, mesenteric fat, retroperitoneal fat and total visceral fat per body weight of mice that were given test diets. Gray bars denote normal diet group (ND), black bars denote high-fat diet control group (HFD), and orange bars denote camphene-administered group. The letters a, b and c exhibit significant difference between test groups at $P<0.001$ by analysis of variance (ANOVA) followed by Duncan's multiple range test.
Figure 4:
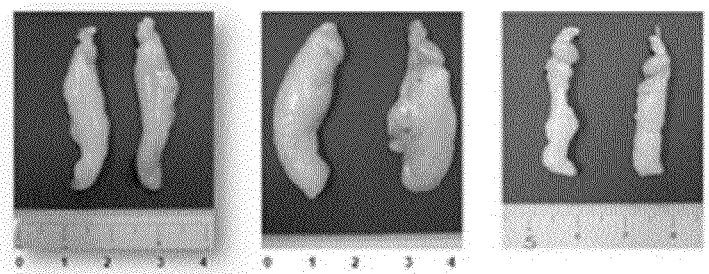
FIG. 4 shows visceral fats of mice that were given test diets from different (epididymal, mesenteric, retroperitoneal and perirenal) parts.
Figure 4:
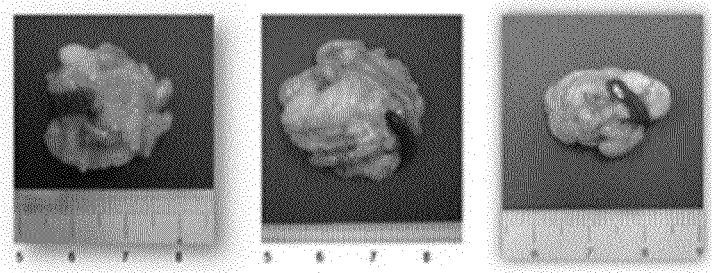
Figure 4:
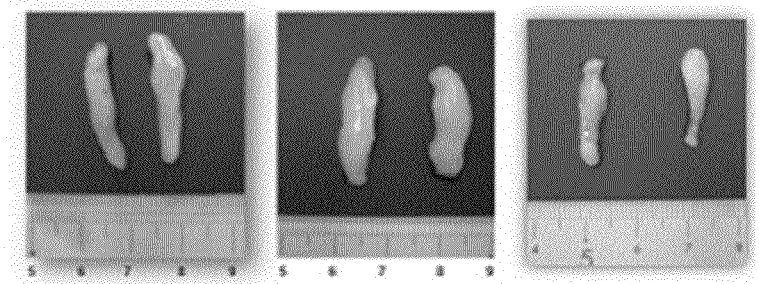
Figure 4:
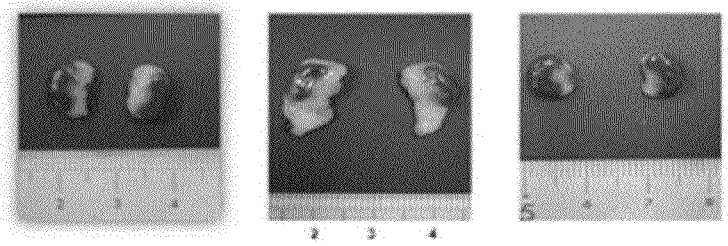

And, when the weight of epididymal fat, perirenal fat, mesenteric fat and retroperitoneal fat per body weight was measured after 10 weeks of feeding the test diets, the camphene-administered group showed significantly lower (P<0.001) epididymal fat weight (46%), perirenal fat weight (76%), mesenteric fat weight (61%), retroperitoneal fat weight (48%) and total visceral fat weight (52%) as compared to the control group (HFD) (see FIGS. 3 and 4). Accordingly, it can be seen that camphene has excellent effect of reducing body weight and visceral fat.

Example 3

Camphene's Effect of Preventing and Treating Obesity-Induced Hyperlipidemia, Fatty Liver and Type 2 Diabetes Total cholesterol, triglyceride and glucose levels in the serum were measured twice for each using a commercially available kit (Bio Clinical system), and insulin level was measured by ELISA using a mouse insulin kit (Shibayaki, Japan). Lipids were extracted from the liver tissue according to Folch et al.'s method. After adding 1 mL of distilled water to 0.25 g of liver tissue, the liver tissue was homogenized using a Polytron homogenizer (IKA-Werke GmbH & Co., Ultra-Turrax, Staufen, Germany). After adding 5 mL of chloroform:methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanol:0.05% CaCl$_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed. The same kit (Bio Clinical system) as the one used for the serum analysis was used to measure the triglyceride level of the liver tissue.

After 10 weeks of feeding the test diets described in Table 1, the camphene-administered group showed significantly lower triglyceride level (69%), total cholesterol level (60%), LDL+VLDL cholesterol level (79%), arteriosclerotic index (59%) and free fatty acid level (86%) as compared to the high-fat diet control group (HFD) (see Table 2). Also, the camphene-administered group showed significantly lower fasting blood sugar level (10%), serum insulin level (32%) and insulin resistance (IRI) (40%) as compared to the high-fat diet control group (HFD) (see Table 2). Accordingly, it can be seen that camphene has effect of improving type 2 diabetes or insulin resistance and metabolic inflammatory response related thereto.

TABLE 2

Obesity-related biochemical indices in blood of camphene-administered mouse

| | Normal diet group (ND) | High-fat die control group (HFD) | Camphene-administered group (Camphene) |
|---|---|---|---|
| Triglyceride (mmol/L) | 0.60 ± 0.09$^b$ | 1.41 ± 0.12$^a$ | 0.44 ± 0.05$^b$ |
| Total cholesterol (mmol/L) | 1.96 ± 0.03$^b$ | 3.83 ± 0.32$^a$ | 1.55 ± 0.11$^b$ |
| HDL cholesterol (mmol/L) | 1.42 ± 0.03$^b$ | 1.78 ± 0.07$^a$ | 1.02 ± 0.04$^c$ |
| LDL + VLDL cholesterol (mmol/L) | 0.54 ± 0.02$^b$ | 2.05 ± 0.25$^a$ | 0.44 ± 0.05$^b$ |
| Arteriosclerotic index[1] | 0.38 ± 0.02$^b$ | 1.02 ± 0.18$^a$ | 0.42 ± 0.03$^b$ |
| Free fatty acid (µEq/L) | 573 ± 40$^b$ | 1417 ± 128$^a$ | 197 ± 6.7$^c$ |
| Glucose (mmol/L) | 6.17 ± 0.95$^b$ | 8.49 ± 0.53$^a$ | 7.6 ± 0.51$^{ab}$ |
| Insulin (ng/mL) | 0.72 ± 0.06$^b$ | 1.26 ± 0.02$^a$ | 0.85 ± 0.23$^b$ |
| IRI[2] | 0.79 ± 0.31$^b$ | 1.84 ± 0.24$^a$ | 1.11 ± 0.21$^b$ |

Different letters within the same row exhibit significant difference at P < 0.05 by one-way ANOVA followed by Duncan's multiple range test.
[1] Arteriosclerotic index = (total cholesterol − HDL cholesterol)/HDL cholesterol
[2] Insulin resistance index (IRI) = $10^{-3}$ pmol insulin × mmol glucose × L$^{-2}$ After 10 weeks of feeding the test diets, the camphene-administered group showed significantly lower liver weight per body weight (22%) as compared to the high-fat diet control group (HFD). Also, the camphene-administered group showed significantly lower triglyceride level (58%), cholesterol level (86%) and free fatty acid level (73%) in the liver tissue as compared to the high-fat diet control group (HFD) (see Table 3). Accordingly, it can be seen that camphene effect of remarkably relieving fatty liver in high-fat diet-induced obesity and remarkably improving obesity-induced inflammations and insulin resistance in the liver tissue.

TABLE 3

Obesity-related biochemical indices in liver tissue of camphene-administered mouse

| | Normal diet group (ND) | High-fat die control group (HFD) | Camphene-administered group (Camphene) |
|---|---|---|---|
| Liver weight (g/100 g body wt) | 3.6 ± 0.14$^b$ | 5.5 ± 0.32$^a$ | 4.3 ± 0.32$^b$ |
| Triglyceride (µmol/g) | 20.3 ± 1.21$^b$ | 35.0 ± 1.22$^a$ | 14.7 ± 2.3$^c$ |
| Cholesterol (µmol/g) | 21.6 ± 0.58$^b$ | 74.8 ± 0.68$^a$ | 10.3 ± 2.6$^c$ |
| Free fatty acid (µEq/g) | 8.6 ± 1.13$^b$ | 24.3 ± 0.86$^a$ | 6.5 ± 0.91$^b$ |

Different letters within the same row exhibit significant difference at P < 0.05 by one-way ANOVA followed by Duncan's multiple range test.

Example 4

Camphene's Effect of Suppressing Expression of Obesity-Related Genes in Mouse Visceral Fat Tissue Extraction of RNA by TRIzol Method and Identification After adding 1 mL of TRIzol solution per 0.1 g of epididymal fat tissue, centrifugation was performed at 4° C. and 12,000×g for 10 minutes. The supernatant was transferred to a fresh tube and vortexed after adding 200 µL of chloroform. After repeating this procedure twice, the supernatant was transferred to a fresh tube and isopropanol was added to the supernatant at a ratio of 1:1. After shaking strongly for 10 times and keeping at room temperature for 10 minutes, centrifugation was performed at 4° C. and 12,000×g for 10 minutes. After removing the supernatant and adding 1 mL of 70% ethanol to the remaining pellets, centrifugation was performed at 4° C. and 7,500×g for 5 minutes. After removing ethanol, the RNA pellets held in the tube were dried at room temperature for 5 minutes and dissolved using nuclease-free water. The concentration of the extracted RNA was measured at 260 nm and 280 nm using a UV/VIS spectrophotometer (Beckman Coulter, DU730), and the integrity of RNA was analyzed by agarose gel electrophoresis.

Reverse Transcription Polymerase Chain Reaction (RT-PCR)

cDNA was synthesized by performing reverse transcription for the RNA sample extracted from the epididymal fat tissue using oligo-dT primer and SuperScript reverse transcriptase (GIBCO BRL, Gaithersburg, Md., USA). Then, PCR was performed using the cDNA obtained through the reverse transcription as template and 5' and 3' flanking sequences of the cDNA gene desired to be amplified as primers. The primer sequences are shown in Table 4. 1 µL of the amplified PCR product was subjected to electrophoresis on 1% agarose gel for identification of DNA bands.

TABLE 4

Primer sequences used for RT-PCR

| Gene | Primer | Sequence (5'→3') | Annealing temp. (° C.) | PCR product (bp) |
|---|---|---|---|---|
| Peroxisome proliferator-activated | F | TTCGGAATCAGCTCTGTGGA | 55 | 148 |
| | R | CCATTGGGTCAGCTCTTGTG | | |

TABLE 4-continued

Primer sequences used for RT-PCR

| Gene | Primer | Sequence (5'→3') | Annealing temp. (° C.) | PCR product (bp) |
|---|---|---|---|---|
| receptor gamma 2 (PPARγ2) | | | | |
| Adipocyte protein 2 (aP2) | F<br>R | AGCATCATAACCCTAGATGG<br>GAAGTCACGCCTTTCATAAC | 55 | 128 |
| CCAAT/enhancer binding protein alpha (C/EBPα) | F<br>R | TCGGTGCGTCTAAGATGAGG<br>TCAAGGCACATTTTTGCTCC | 55 | 187 |
| TNF-alpha (TNFα) | F<br>R | TGTCTCAGCCTCTTCTCATT<br>AGATGATCTGAGTGTGAGGG | 55 | 156 |
| Interleukin 6 (IL-6) | F<br>R | ATGAAGTTCCTCTCTGCAAGAGACT<br>CACTAGGTTTGCCGAGTAGATCTC | 55 | 638 |
| Uncoupling protein 1 (UCP1) | F<br>R | GGGACCTACAATGCTTACAG<br>GGTCATATGTCACCAGCTCT | 55 | 103 |
| Uncoupling protein 3 (UCP3) | F<br>R | ACGGATGTGGTGAAGGTCCG<br>TACAAACATCATCACGTTCC | 55 | 464 |
| Glyceraldehyde 3-phosphate dehydrogenase (GAPDH) | F<br>R | AGAACATCATCCCTGCATCC<br>TCCACCACCCTGTTGCTGTA | 55 | 321 |

RT-PCR Result for Epididymal Fat Tissue

Adipogenesis is the process of cell differentiation by which preadipocytes grow and differentiate into mature adipocytes, accompanied by morphological changes and changes in gene expression pattern. During the process, lipids are accumulated and adipose-specific genes such as fatty acid binding protein (aP2), lipoprotein lipase (LPL) and adipsin are expressed. The expression of such genes is regulated by three transcription factors called peroxisome proliferator activated receptor gamma (PPARγ), CCAAT enhancer-binding proteins (C/EBPs) and sterol regulatory binding protein-1c (SREBP-1c).

Figure 5A:
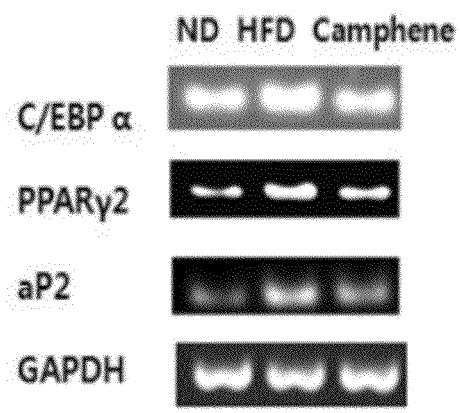
FIGS. 5a-5b show the change in expression of adipogenesis-related genes in mouse visceral fat tissue.
Figure 5B:
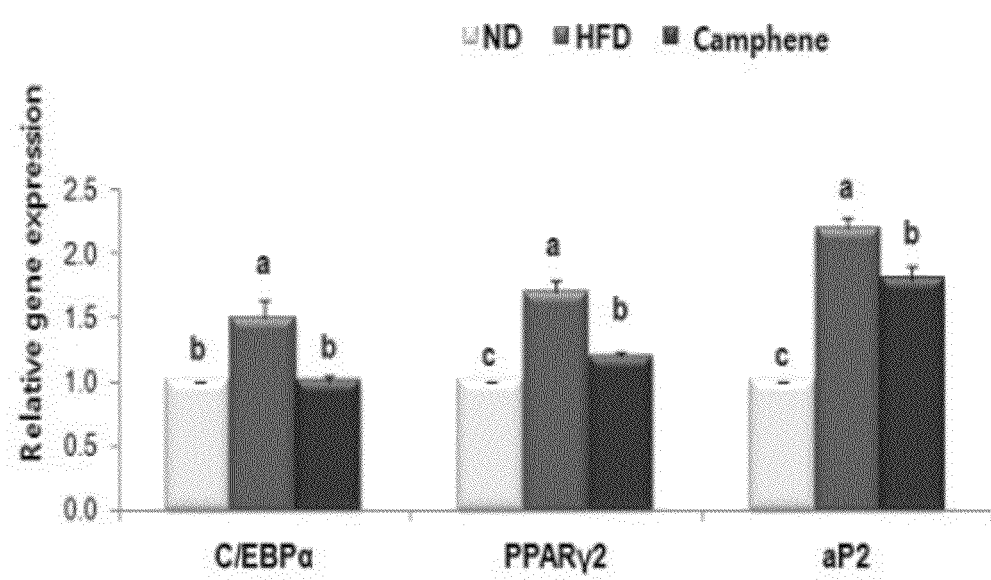

As a result of analyzing the degree of mRNA expression in epididymal fat tissue by RT-PCR, the high-fat diet control group (HFD) showed significant increase in the expression of the nuclear transcription factors C/EBPα and PPARγ2 playing important roles in adipogenesis and their target gene aP2, as compared to the normal diet group (ND). Meanwhile, the camphene-administered group showed significantly decreased expression of the nuclear transcription factors (C/EBPα and PPARγ2) and their target gene (aP2) in the visceral fat tissue, as compared to the high-fat diet group (FIGS. 5a and 5b). Therefore, it can be seen that the administration of camphene reduced visceral fat by decreasing the expression of the nuclear transcription factors playing pivotal roles in adipogenesis and their target gene in the visceral fat tissue.

Recently, the term 'metaflammation' was coined to refer to inflammatory response triggered by oversupply of nutrients or metabolites, and obesity was considered as 'chronic and low-level inflammation'. Like these, researches on the relationship between obesity and the immune system have been intensively made. For instance, toll-like receptor 4 (TLR4) associated with innate immune response plays an important role in inflammatory response and insulin resistance pathway using dietary fatty acid (particularly, saturated fatty acid) as a ligand, and is also related to regulation of food intake in the central nervous system. It is known that obesity induced by high-fat diet leads to increased level of free fatty acid (particularly, saturated fatty acid) in the body fluid. When the free fatty acid is bound to TLR4 as a ligand, it activates IKK, thereby activating NF-κB and promoting secretion of pro-inflammatory cytokines TNF-α, IL-6, etc., thus leading to inflammatory response. Besides, TNF-α and IL-6 are known to activate suppressor of cytokine signaling 3 (SOCS3) and JNK, thereby inhibiting phosphorylating the serine residue of insulin receptor substrate (IRS) and thus inhibiting glucose transport and inducing insulin resistance in peripheral tissues such as liver, muscle, etc.

Figure 6A:
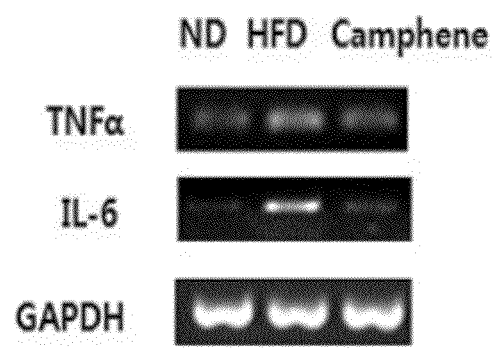
FIG. 6a-6b show the change in expression of inflammation-related genes in mouse visceral fat tissue.
Figure 6B:
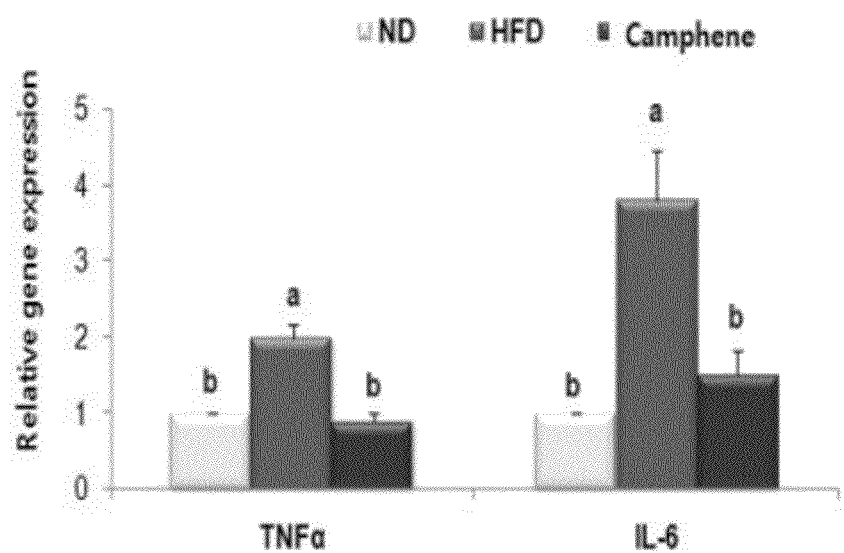

As a result of evaluating the degree of expression of the mRNA of the cytokines that activate inflammatory response in visceral fat tissue by RT-PCR, the HFD group showed significantly increased expression of TNFα and IL-6 genes as compared to the ND group. In contrast, the camphene-administered group showed decreased expression of TNFα and IL-6 genes back to the level of the ND group (FIGS. 6a and 6b). Accordingly, it can be seen that camphene has remarkable effect of improving chronically activated inflammation in the visceral fat tissue induced by obesity.

Mitochondrial dysfunction is known to be associated with aging, heart diseases, gastroenteric disorder, endocrine disorder or nerve disorder. It is also known that disorders in mitochondrial oxidation may lead to fatty liver by increasing glucose production in the liver tissue and thus inducing hyperglycemia. Mitochondria form a proton gradient between the inner membrane and outer membrane of the mitochondria via the electron transport chain, and produce ATP with the aid of F0F1-ATPase with it as the driving force. When F0F1-ATPase does not function normally, the proton gradient is reduced by uncoupling proteins (UCPs) and heat is generated during this process. Recently, with the report that the UCPs facilitate heat generation while maintaining redox balance via such energy-dissipatory mechanism, they are drawing attentions as a new target for treatment of obesity along with AMPK.

Figure 7:
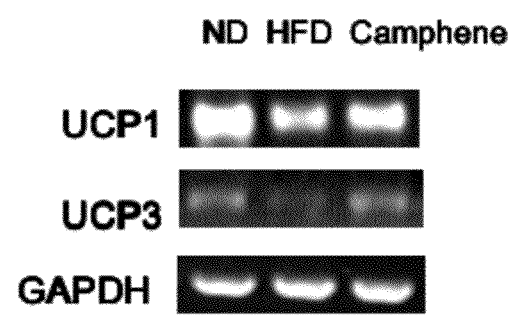
FIG. 7 shows the change in expression of UCP genes in mouse visceral fat tissue.

As a result of extracting mRNA from the mouse visceral fat tissue that had been given the test diets and measuring the expression of UCP1 and UCP3 by RT-PCR, the HFD group showed significantly reduced expression of UCP1 and UCP3 genes as compared to the ND group. In contrast, the camphene-administered group showed increased expression of UCP1 and UCP3 genes (FIG. 7). Accordingly, it can be seen that the administration of camphene has remarkable effect of improving suppressed heat generation in the visceral fat tissue induced by obesity.

The features and advantages of the present disclosure can be summarized as follows.

(i) The present disclosure provides a composition comprising camphene as an active ingredient for preventing or treating obesity, dyslipidemia, fatty liver or insulin resistance syndrome.

(ii) The active ingredient of the composition of the present disclosure can be isolated from various plants or can be synthesized chemically.

(iii) The composition of the present disclosure comprising camphene as an active ingredient suppresses differentiation of adipocytes, reduces body fat, reduces visceral fat, reduces total cholesterol level, reduces serum triglyceride level and reduces liver tissue triglyceride level, and thus exhibits preventive or therapeutic activity for obesity, hyperlipidemia or fatty liver. Furthermore, the composition of the present disclosure exhibits the effect of improving type 2 diabetes or insulin resistance and related metabolic disease by significantly reducing fasting blood sugar level and blood insulin level.

(iv) Also, the composition of the present disclosure exhibits the effect of reducing visceral fat by significantly reducing the expression of nuclear transcription factors (C/EBPα and PPARγ2) playing key roles in adipogenesis or their target gene (aP2), the effect of improving chronically activated inflammation in the visceral fat tissue induced by obesity by significantly reducing the expression of cytokines (TNF-α or IL-6) activating inflammation, and the effect of improving suppressed heat generation in the visceral fat tissue induced by obesity by significantly increasing the expression of UCP (UCP1 or UCP3) genes regulating body heat production.

While the present disclosure has been described with respect to the specific embodiments, it will be apparent to those skilled in the art that various changes and modifications may be made without departing from the spirit and scope of the disclosure as defined in the following claims.

What is claimed is:

1. A method for treating a metabolic disease selected from the group consisting of obesity, dyslipidemia, fatty liver and insulin resistance syndrome, comprising administering a composition comprising isolated or synthesized camphene as an active ingredient to a subject.

2. The method according to claim 1, wherein the dyslipidemia is hyperlipidemia.

3. The method according to claim 1, wherein the insulin resistance syndrome comprises one or more disease selected from the group consisting of obesity, hypertension, arteriosclerosis, hyperlipidemia, hyperinsulinemia, non-alcoholic fatty liver and type 2 diabetes caused by insulin resistance.

4. The method according to claim 1, wherein the treatment is to reduce the differentiation of adipocytes.

5. The method according to claim 1, wherein the treatment is to reduce the level of fats in the serum or liver or to reduce the visceral fat mass.

6. The method according to claim 5, wherein the fat comprises triglyceride, cholesterol or free fatty acid.

7. The method according to claim 5, wherein the visceral fat comprises one or more fat selected from epididymal fat, perirenal fat, mesenteric fat and retroperitoneal fat.

8. The method according to claim 1, wherein the treatment is to reduce the glucose level in the serum.

9. The method according to claim 1, wherein the treatment is to reduce the insulin level in the serum.

10. The method according to claim 1, wherein the composition is a pharmaceutical composition or a food composition.

11. The method according to claim 1, wherein the camphene is derived from a camphene-containing plant.

12. The method according to claim 1, wherein the composition reduces the expression of CCAAT/enhancer binding protein alpha (C/EBPα), peroxisome proliferator-activated receptor gamma 2 (PPARγ2) or adipocyte protein 2 (aP2).

13. The method according to claim 1, wherein the composition reduces the expression of tumor necrosis factor-alpha (TNF-α) or interleukin-6 (IL-6).

14. The method according to claim 1, wherein the composition increases the expression of uncoupling protein 1 (UCP1) or uncoupling protein 3 (UCP3).

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Forward primer of peroxisome proliferator
      activated receptor gamma 2

<400> SEQUENCE: 1
ttcggaatca gctctgtgga                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer of peroxisome proliferator
      activated receptor gamma 2

<400> SEQUENCE: 2
ccattgggtc agctcttgtg                                              20

<210> SEQ ID NO 3
<211> LENGTH: 20
<212> TYPE: DNA
<213> ORGANISM: Artificial Sequence
<220> FEATURE:
<223> OTHER INFORMATION: Forward primer of adipocyte protein2

<400> SEQUENCE: 3
agcatcataa ccctagatgg                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse primer of adipocyte protein2
```

```
<400> SEQUENCE: 4
gaagtcacgc ctttcataac                                          20

<210> SEQ ID NO 5
<211> LENGTH: 20
<212> TYPE: DNA
<213> ORGANISM: Artificial Sequence
<220> FEATURE:
<223> OTHER INFORMATION: Forward primer of CCAAT/enhancer binding
      protein alpha

<400> SEQUENCE: 5
tcggtgcgtc taagatgagg                                          20

<210> SEQ ID NO 6
<211> LENGTH: 20
<212> TYPE: DNA
<213> ORGANISM: Artificial Sequence
<220> FEATURE:
<223> OTHER INFORMATION: Reverse primer of CCAAT/enhancer binding
      protein alpha

<400> SEQUENCE: 6
tcaaggcaca ttttttgctcc                                         20

<210> SEQ ID NO 7
<211> LENGTH: 20
<212> TYPE: DNA
<213> ORGANISM: Artificial Sequence
<220> FEATURE:
<223> OTHER INFORMATION: Forward primer of TNF-alpha

<400> SEQUENCE: 7
tgtctcagcc tcttctcatt                                          20

<210> SEQ ID NO 8
<211> LENGTH: 20
<212> TYPE: DNA
<213> ORGANISM: Artificial Sequence
<220> FEATURE:
<223> OTHER INFORMATION: Reverse primer of TNF-alpha

<400> SEQUENCE: 8
agatgatctg agtgtgaggg                                          20

<210> SEQ ID NO 9
<211> LENGTH: 25
<212> TYPE: DNA
<213> ORGANISM: Artificial Sequence
<220> FEATURE:
<223> OTHER INFORMATION: Forward primer of Interleukin 6

<400> SEQUENCE: 9
atgaagttcc tctctgcaag agact                                    25

<210> SEQ ID NO 10
<211> LENGTH: 24
<212> TYPE: DNA
<213> ORGANISM: Artificial Sequence
<220> FEATURE:
<223> OTHER INFORMATION: Reverse primer of Interleukin 6

<400> SEQUENCE: 10
cactaggttt gccgagtaga tctc                                     24

<210> SEQ ID NO 11
```

```
<211> LENGTH: 20
<212> TYPE: DNA
<213> ORGANISM: Artificial Sequence
<220> FEATURE:
<223> OTHER INFORMATION: Forward primer of uncoupling protein 1

<400> SEQUENCE: 11
gggacctaca atgcttacag                                              20

<210> SEQ ID NO 12
<211> LENGTH: 20
<212> TYPE: DNA
<213> ORGANISM: Artificial Sequence
<220> FEATURE:
<223> OTHER INFORMATION: Reverse primer of uncoupling protein 1

<400> SEQUENCE: 12
ggtcatatgt caccagctct                                              20

<210> SEQ ID NO 13
<211> LENGTH: 20
<212> TYPE: DNA
<213> ORGANISM: Artificial Sequence
<220> FEATURE:
<223> OTHER INFORMATION: Forward primer of uncoupling protein 3

<400> SEQUENCE: 13
acggatgtgg tgaaggtccg                                              20

<210> SEQ ID NO 14
<211> LENGTH: 20
<212> TYPE: DNA
<213> ORGANISM: Artificial Sequence
<220> FEATURE:
<223> OTHER INFORMATION: Reverse primer of uncoupling protein 3

<400> SEQUENCE: 14
tacaaacatc atcacgttcc                                              20

<210> SEQ ID NO 15
<211> LENGTH: 20
<212> TYPE: DNA
<213> ORGANISM: Artificial Sequence
<220> FEATURE:
<223> OTHER INFORMATION: Forward primer of Glyceraldehyde-3-
      phosphatedehydrogenase

<400> SEQUENCE: 15
agaacatcat ccctgcatcc                                              20

<210> SEQ ID NO 16
<211> LENGTH: 20
<212> TYPE: DNA
<213> ORGANISM: Artificial Sequence
<220> FEATURE:
<223> OTHER INFORMATION: Reverse primer of Glyceraldehyde-3-
      phosphatedehydrogenase

<400> SEQUENCE: 16
tccaccaccc tgttgctgta                                              20
```